United States Patent
Loick et al.

(10) Patent No.: US 10,427,135 B2
(45) Date of Patent: Oct. 1, 2019

(54) AMINOPOLYCARBOXYLIC ACIDS USEFUL AS PROCESSING AIDS IN THE MANUFACTURE OF SUPERABSORBENTS

(71) Applicant: EVONIK DEGUSSA GMBH, Essen (DE)

(72) Inventors: Christoph Loick, Tönisvorst (DE); Ingo Loy, Krefeld (DE); Dominik Gartz, Viersen (DE)

(73) Assignee: Evonik Degussa GmbH, Essen (DE)

( * ) Notice: Subject to any disclaimer, the term of this patent is extended or adjusted under 35 U.S.C. 154(b) by 313 days.

(21) Appl. No.: 14/848,547

(22) Filed: Sep. 9, 2015

(65) Prior Publication Data

US 2016/0074832 A1    Mar. 17, 2016

Related U.S. Application Data

(60) Provisional application No. 62/050,270, filed on Sep. 15, 2014.

(30) Foreign Application Priority Data

Sep. 15, 2014   (EP) .................................... 14184703

(51) Int. Cl.
| | |
|---|---|
| *B01J 20/30* | (2006.01) |
| *C08F 2/44* | (2006.01) |
| *C08F 6/00* | (2006.01) |
| *C08L 101/14* | (2006.01) |
| *A61L 15/24* | (2006.01) |
| *B01J 20/26* | (2006.01) |
| *A61L 15/60* | (2006.01) |

(52) U.S. Cl.
CPC ........... *B01J 20/3085* (2013.01); *A61L 15/24* (2013.01); *A61L 15/60* (2013.01); *B01J 20/261* (2013.01); *B01J 20/267* (2013.01); *B01J 20/3014* (2013.01); *C08F 2/44* (2013.01); *C08F 6/008* (2013.01); *C08L 101/14* (2013.01)

(58) Field of Classification Search
CPC combination set(s) only.
See application file for complete search history.

(56) References Cited

U.S. PATENT DOCUMENTS

| | | | |
|---|---|---|---|
| 4,666,983 A | 5/1987 | Tsubakimoto et al. | |
| 4,734,478 A | 3/1988 | Tsubakimoto et al. | |
| 5,004,761 A | 4/1991 | Yada et al. | |
| 5,331,059 A | 7/1994 | Engelhardt et al. | |
| 5,409,771 A | 4/1995 | Dahmen et al. | |
| 5,837,789 A | 11/1998 | Stockhausen et al. | |
| 6,143,821 A | 11/2000 | Houben | |
| 6,239,230 B1 | 5/2001 | Eckert et al. | |
| 6,241,928 B1 | 6/2001 | Hatsuda et al. | |
| 6,472,478 B1 | 10/2002 | Funk et al. | |
| 6,503,979 B1 | 1/2003 | Funk et al. | |
| 6,559,239 B1 | 5/2003 | Riegel et al. | |
| 6,657,015 B1 | 12/2003 | Riegel et al. | |
| 6,710,141 B1 | 3/2004 | Heide et al. | |
| 6,939,991 B2 | 9/2005 | Thiel et al. | |
| 7,183,360 B2 | 2/2007 | Daniel et al. | |
| 7,199,211 B2 | 4/2007 | Popp et al. | |
| 7,250,481 B2 | 7/2007 | Jaworek et al. | |
| 7,259,212 B2 | 8/2007 | Popp et al. | |
| 7,405,321 B2 | 7/2008 | Riegel et al. | |
| 7,420,013 B2 | 9/2008 | Riegel et al. | |
| 7,557,245 B2 | 7/2009 | Nordhoff et al. | |
| 7,652,111 B2 | 1/2010 | Hermeling et al. | |
| 7,687,596 B2 | 3/2010 | Hermeling et al. | |
| 7,754,822 B2 | 7/2010 | Daniel et al. | |
| 7,772,420 B2 | 8/2010 | Hermeling et al. | |
| 7,803,969 B2 | 9/2010 | Nordhoff et al. | |
| 7,964,689 B2 | 6/2011 | Nordhoff et al. | |
| 8,013,087 B2 | 9/2011 | Loesch et al. | |
| 8,183,331 B2 | 5/2012 | Loesch et al. | |
| 8,420,567 B1 | 4/2013 | Naumann et al. | |
| 8,476,189 B1 | 7/2013 | Naumann et al. | |
| 8,859,701 B2 | 10/2014 | Loick et al. | |
| 8,865,828 B2 | 10/2014 | Daniel et al. | |
| 2004/0145964 A1* | 7/2004 | Kunz | B01F 7/00208 366/97 |
| 2004/0186229 A1 | 9/2004 | Heide et al. | |
| 2005/0165208 A1 | 7/2005 | Popp et al. | |
| 2006/0212011 A1 | 9/2006 | Popp et al. | |
| 2011/0224361 A1* | 9/2011 | Daniel | C08F 220/06 524/556 |

(Continued)

FOREIGN PATENT DOCUMENTS

| | | |
|---|---|---|
| CN | 104039847 A | 9/2014 |
| DE | 3314019 A1 | 1/1984 |

(Continued)

OTHER PUBLICATIONS

German language European Search Report dated Mar. 17, 2015 in EP 14184703.8 (7 pages).

(Continued)

*Primary Examiner* — Nicole M. Buie-Hatcher
(74) *Attorney, Agent, or Firm* — Bernard Lau; Linda S. Li; Jason S. Ngui

(57) ABSTRACT

Described is the production of water-absorbing polymeric particles by polymerizing a monomer solution or suspension comprising a) at least one ethylenically unsaturated acid-functional monomer which is optionally at least partly present as salt, b) at least one crosslinker and c) at least one initiator, wherein the process further comprises drying the resulting polymer and also optionally grinding the dried polymer and sieving the ground polymer and also optionally surface-postcrosslinking the dried and possibly ground and sieved polymer, and wherein the polymerization is carried out in the presence of aminopolycarboxylic acids and/or salts thereof, in particular in the presence of ethylenediaminedisuccinic acid and/or a salt thereof.

9 Claims, No Drawings

(56) References Cited

U.S. PATENT DOCUMENTS

| | | | |
|---|---|---|---|
| 2011/0306732 A1* | 12/2011 | Fujino | C08F 2/44 525/385 |
| 2012/0145956 A1 | 6/2012 | Walden | |
| 2012/0289671 A1* | 11/2012 | Takaai | A61L 15/60 526/240 |
| 2014/0054497 A1 | 2/2014 | Wattebled et al. | |
| 2014/0114035 A1* | 4/2014 | Nogi | C08J 3/12 526/212 |
| 2014/0257223 A1 | 9/2014 | Henn et al. | |
| 2015/0093575 A1 | 4/2015 | Naumann et al. | |
| 2015/0252130 A1 | 9/2015 | Loick et al. | |

FOREIGN PATENT DOCUMENTS

| | | |
|---|---|---|
| DE | 3523617 A1 | 1/1986 |
| DE | 3713601 A1 | 11/1988 |
| DE | 3825366 A1 | 2/1989 |
| DE | 4020780 C1 | 8/1991 |
| DE | 19543368 A1 | 5/1997 |
| DE | 19646484 A1 | 5/1997 |
| DE | 19807992 C1 | 7/1999 |
| DE | 19807502 A1 | 9/1999 |
| DE | 19854573 A1 | 5/2000 |
| DE | 19854574 A1 | 5/2000 |
| DE | 10204937 A1 | 8/2003 |
| DE | 10204938 A1 | 8/2003 |
| DE | 10331450 A1 | 1/2005 |
| DE | 10331456 A1 | 2/2005 |
| DE | 10334584 A1 | 2/2005 |
| DE | 10355401 A1 | 6/2005 |
| EP | 0083022 A2 | 7/1983 |
| EP | 0450922 A2 | 10/1991 |
| EP | 0530438 A1 | 3/1993 |
| EP | 0547847 A1 | 6/1993 |
| EP | 0559476 A1 | 9/1993 |
| EP | 0632068 A1 | 1/1995 |
| EP | 0937736 A2 | 8/1999 |
| EP | 1199327 A2 | 4/2002 |
| EP | 2116571 A1 | 11/2009 |
| EP | 2208756 A1 | 7/2010 |
| EP | 2727953 A1 | 5/2014 |
| JP | 2015503655 A | 2/2015 |
| WO | 9015830 A1 | 12/1990 |
| WO | 9321237 A1 | 10/1993 |
| WO | 2001038402 A1 | 5/2001 |
| WO | 2002055469 A1 | 7/2002 |
| WO | 2003031482 A1 | 4/2003 |
| WO | 2003078378 A1 | 9/2003 |
| WO | 2003104299 A1 | 12/2003 |
| WO | 2003104300 A1 | 12/2003 |
| WO | 2003104301 A1 | 12/2003 |
| WO | 2004035514 A1 | 4/2004 |
| WO | 2008040715 A2 | 4/2008 |
| WO | 2008052971 A1 | 5/2008 |
| WO | 2010057912 A1 | 5/2010 |

OTHER PUBLICATIONS

Loick et al., U.S. Appl. No. 14/808,012, filed Jul. 24, 2015.
Loick et al., U.S. Appl. No. 14/848,483, filed Sep. 9, 2015.

* cited by examiner

AMINOPOLYCARBOXYLIC ACIDS USEFUL AS PROCESSING AIDS IN THE MANUFACTURE OF SUPERABSORBENTS

This application claims the benefit of U.S. Provisional Application No. 62/050,270 filed on Sep. 15, 2014 and European Application No. 14184703.8 filed on Sep. 15, 2014, the disclosures of which are expressly incorporated herein by reference.

FIELD

The present invention resides in the field of superabsorbents and water-absorbing polymeric particles. The present invention relates particularly to a process for producing water-absorbing polymeric particles by use of specified aminopolycarboxylic acids and/or salts thereof. The present invention relates to water-absorbing polymeric particles, hygiene articles comprising water-absorbing polymeric particles and also the use of specified aminopolycarboxylic acids and/or salts thereof as processing aids in the manufacture of water-absorbing polymeric particles.

BACKGROUND

Superabsorbents are known, the term designating crosslinked hydrophilic polymers capable of imbibing large amounts of aqueous fluids. This capability rests on the strong interaction of water with hydrophilic groups on the superabsorbents, in particular ionic groups or groups capable of hydrogen bonding. Other customary designations for what are known as superabsorbents include "superabsorbent polymer", "hydrogel" (often even used for the dry form), "hydrogen-forming polymer", "water-absorbing polymer", "absorbent gel-forming material", "swellable resin", "water-absorbing resin" or the like. Water-absorbing polymers based on partially neutralized acrylic acid are concerned in particular. The essential properties of superabsorbents are their ability to absorb a multiple (30-800 times for example) of their own weight of aqueous fluids and to retain the fluid even under some pressure. The superabsorbent, which is used in the form of a dry powder, turns into a gel on imbibing liquid, and so turns into a hydrogel when, as typical, imbibing water. Crosslinking is essential for synthetic superabsorbents and renders the polymers insoluble in water. Soluble substances would not be useful as superabsorbents. By far the most important field of use for superabsorbents is that of absorbing bodily fluids. Superabsorbents are used, for example, in diapers for infants, incontinence products for adults or femcare products. Fields of use further include, for example, as a water-retaining agent in market gardening, as a water storage medium for protection against fire, for fluid absorption in food packaging, as cable cladding material for deep sea cables or, very generally, for absorption of moisture.

Such a superabsorbent in general has a CRC ("Centrifuge Retention Capacity") of at least 5 g/g, preferably at least 10 g/g, more preferably at least 20 g/g, especially 30 g/g. It is not just its absorption capacity which is important for a superabsorbent, but also its retention (ability to retain liquid under pressure usually expressed as "Absorption against Pressure" ("AAP")) and also its permeability, i.e. the ability to conduct liquid in the swollen state. Flow conductivity to as yet unswollen superabsorbent may be blocked by swollen gel ("gel blocking"). Good conductivity properties for liquids are shown, for example, by hydrogels that have a high level of gel strength in the swollen state. Gels having only low gel strength are deformable under an applied pressure (body pressure), cause pores to clog in a superabsorbent/cellulose fiber pad and thereby block flow conductivity to as yet unswollen or incompletely swollen superabsorbent and the imbibition of liquid by this, as yet unswollen or incompletely swollen superabsorbent. Elevated gel strength is generally achieved through a relatively high level of crosslinking, but this reduces the absorption capacity of the product. A standard method of increasing gel strength is to increase the level of crosslinking at the surface of the superabsorbent particles compared to the interior of the particles. To this end, in a surface postcrosslinking step, dried superabsorbent particles having an average crosslinking density are subjected to additional crosslinking in a thin surface layer of the particles. Surface postcrosslinking increases the crosslink density in the shell of the superabsorbent particles, raising the absorption under confining pressure to a higher level. While the absorption capacity in the surface layer of the superabsorbent particles decreases, the presence of mobile chains of polymer in their core leads to an improved absorption capacity compared with the shell, so shell construction ensures an improved permeability without occurrence of gel blocking. It is likewise known to produce comparatively highly crosslinked superabsorbents overall and to subsequently reduce the degree of crosslinking in the interior of the particles versus an outer shell of the particles.

The manufacture of such superabsorbents (also called superabsorbent polymers) is based essentially on the polymerization of ethylenically unsaturated acid-functional monomers which are optionally at least partly present as a salt, in particular on the free-radical polymerization of partially neutralized acrylic acid, typically in the presence of crosslinkers. A free-radical polymerization reaction is a fast reaction and a strongly exothermic process.

This reaction leads to the construction of a three-dimensional polymeric network which may have different macroscopic properties, depending on process conditions and reaction procedure. When, for example, the polymerization reaction takes place within a very short time accompanied by very considerable evolution of heat, defects may develop in the three-dimensional polymeric network, for example as a consequence of chain transfer reactions, to have an adverse effect on some superabsorbent properties. The uncrosslinked, so-called soluble, fractions may be increased, for example.

If, however, the reaction takes place too slowly, for example as a result of flawed initiation or incorrect temperature management there may for example be a significant increase in the so-called residual monomer fractions due to insufficient conversion.

In principle, there are different ways to control the polymerization kinetics. For instance, monomer, initiator and crosslinker composition and concentration can be used to influence the kinetics. Owing to the large effect of polymerization kinetics on product quality there is a continuous demand for ways to control the polymerization kinetics.

The problem addressed by the present invention against this background was specifically that of controlling the kinetics of the polymerization of ethylenically unsaturated acid-functional monomers, which optionally at least in part are present in the form of a salt, in the manufacture of water-absorbing polymeric particles.

SUMMARY

In aminopolycarboxylic acids and/or salts thereof, in particular in ethylenediaminedisuccinic acid and/or its salt, have now surprisingly been found a particularly efficacious processing aid to control the kinetics of the polymerization of ethylenically unsaturated acid-functional monomers, which optionally are at least partly present in the form of a salt, in particular the polymerization of acrylic acid, which is at least partly present as sodium acrylate in the manufacture of water-absorbing polymeric particles and thereby permit effective influence over the properties of the water-absorbing polymeric particles. A particularly effective way to achieve optimized properties for the water-absorbing polymeric particles is made available as a result.

The problem addressed by the present invention is accordingly solved by a process for producing water-absorbing polymeric particles by polymerizing a monomer solution or suspension comprising
  a) at least one ethylenically unsaturated acid-functional monomer which is optionally present at least partly in salt form,
  b) at least one crosslinker,
  c) at least one initiator,
  d) optionally one or more ethylenically unsaturated monomers copolymerizable with the monomers recited under a),
  e) optionally one or more water-soluble polymers,
  f) water,
  g) optionally additives and/or active substances,
wherein said process further comprises drying the polymer obtained and also optionally grinding the dried polymer and sieving the ground polymer and also optionally surface-postcrosslinking the dried and possibly ground and sieved polymer, and also further optionally aftertreating the possibly surface-postcrosslinked polymer with at least one aftertreating agent, wherein the polymerization is carried out in the presence of a chelating agent from the group of aminopolycarboxylic acids, preferably comprising ethylenediaminedisuccinic acid, ethylenediaminetetraacetic acid, diethylenetriaminetetraacetic acid, glutamic acid N,N diacetic acid, methylglycinediacetic acid, and/or salts thereof, wherein ethylenediaminedisuccinic acid and/or a salt thereof are particularly preferable.

DETAILED DESCRIPTION

The use of aminocarboxylic acids, in particular ethylenediaminedisuccinic acid, ethylenediaminetetraacetic acid, diethylenetriaminetetraacetic acid, glutamic acid N,N diacetic acid, methylglycinediacetic acid, and/or salts thereof, wherein ethylenediaminedisuccinic acid and/or a salt thereof are preferable, can be used to attain inhibition of the polymerization reaction, making optimization of polymer network formation possible, so that improved properties become attainable particularly as regards soluble fractions, CRC and AAP ratio. The degree of this inhibition is simple to adjust via the quantity which is used of aminopolycarboxylic acid and/or its salt, preferably ethylenediaminedisuccinic acid and/or a salt thereof, providing a simple way to control the polymerization kinetics. A person skilled in the art only needs a few range-finding tests for this.

The present invention further enables an improvement in gel processing, in particular in regards to gel comminution, gel transportation and also gel drying, since gel tackiness is reduced and, in particular, minimized.

Aminopolycarboxylic acids useful in the present invention and/or salts thereof are known per se to a person skilled in the art and are readily available commercially. The aminopolycarboxylic acid salt is preferably an alkali metal salt, an alkaline earth metal salt, an ammonium salt, a substituted ammonium salt and/or a mixture thereof, and preferably is a sodium salt.

The use of ethylenediaminedisuccinic acid and/or a salt thereof is very particularly preferable in the context of this invention and corresponds to a particularly preferred embodiment of the present invention.

Ethylenediaminedisuccinic acid (ethylenediaminedisuccinate) has two chiral centers, so it can occur in three different stereoisomers, as (S,S)-, as (R,R)- and as meso-EDDS. The addition of ethylenediamine onto maleic anhydride is an example of a simple route to EDDS that is simple to manage on a large industrial scale. This route leads in fact to a stereoisomeric mixture consisting of the (S,S) and the (R,R) isomer and also the (R,S) isomer (=meso form). An example of a specific synthesis for (S,S)-EDDS consists in the reaction of L-aspartic acid with 1,2-dibromoethane. All three stereoisomers are each singly useful for the purposes of the present invention as are any stereoisomeric mixtures. The use of (S,S)-EDDS is preferable.

Ethylenediaminedisuccinic acid and/or a salt thereof can be used in the present invention. In principle, from 1 to 4 carboxyl groups of ethylenediaminedisuccinic acid can be present in salt form. Mono-, di-, tri- or tetrasalts are obtainable for example. The counter-ion in the salts is the ion of the corresponding base used. Mono-, di-, tri- and tetrasodium salts of EDDS are obtainable on using sodium carbonate or sodium hydroxide for example. Using the corresponding potassium compounds gives the corresponding potassium salts etc. Product mixtures may on average also have odd-numbered values for the number of salt groups in the molecule.

The salt of ethylenediaminedisuccinic acid is preferably an alkali metal salt, an alkaline earth metal salt, an ammonium salt, a substituted ammonium salt and/or a mixture thereof, preferably a sodium salt, especially the tetrasodium salt. "EDDS" herein is to be understood as meaning ethylenediaminedisuccinic acid and/or a salt thereof.

Ethylenediaminetetraacetic acid, diethylenetriaminetetraacetic acid, glutamic acid N,N diacetic acid, methylglycinediacetic acid and/or salts thereof are well known to a person skilled in the art and therefore require no further elucidation. Especially the alkali metal salts concerned can be used with advantage.

What the use of aminopolycarboxylic acids and/or salts thereof, in particular ethylenediaminedisuccinic acid and/or a salt thereof, in the manner of the present invention makes possible in particular is to influence the heat evolution in the polymerization to preferably reduce the heat evolution in the starting phase after initiation of the polymerization, preferably in the first 600 seconds following initiation of the polymerization. The use of aminopolycarboxylic acids and/or salts thereof, in particular ethylenediaminedisuccinic acid and/or a salt thereof, in the manner of the present invention advantageously makes it possible to reduce the uncrosslinked soluble fractions in the polymerization end product, to improve the CRC/AAP ratio in the polymerization end product and also to improve the gel flowability of the undried polymer.

The use of ethylenediaminedisuccinic acid and/or a salt thereof leads in each case to very particularly advantageous results for this invention.

The addition of the chelating agent according to the present invention, i.e. the addition of aminopolycarboxylic acids and/or salts thereof, in particular ethylenediaminedisuccinic acid and/or its salt, may take place before and/or during the polymerization, in one preferred embodiment of the invention. More particularly, the aminopolycarboxylic acid and/or its salt, preferably ethylenediaminedisuccinic acid and/or its salt, may be added before the initiation of the polymerization, to the monomer solution or suspension to be polymerized.

The chelating agent of the present invention, i.e. aminopolycarboxylic acid and/or its salt, preferably ethylenediaminedisuccinic acid and/or its salt, may be added in a solid, particulate form and/or in the form of a preferably aqueous solution to the monomer solution or suspension, in one preferred embodiment of the invention. The addition in the form of an aqueous solution is preferable.

The amounts used of chelating agents according to the present invention, i.e. the amounts used of aminopolycarboxylic acid and/or its salt, preferably ethylenediaminedisuccinic acid and/or its salt, may each be chosen according to the individual requirements of the particular given processing conditions and reaction ratios, in which case a person skilled in the art is able to use a few range-finding tests to establish the desired reaction kinetics entirely as required.

It amounts to a preferred embodiment of the invention for chelating agents according to the present invention, i.e. aminopolycarboxylic acid and/or its salt, preferably ethylenediaminedisuccinic acid and/or its salt, to be added to the monomer solution or suspension in an overall amount of at least 5 ppm, preferably from 50 to 2000 ppm, in particular from 100 to 1500 ppm, based on the amount of unneutralized monomer. The aforementioned amounts make particularly effective control of reaction kinetics possible and, more particularly, a desired temporal slowing of the polymerization initiation phase is achievable.

The present invention makes possible the control of polymerization kinetics in the manufacture of superabsorbent polymers comprising the polymerization of ethylenically unsaturated acid-functional monomers which are optionally at least partly present in the form of a salt.

The potency of the processing aid according to the present invention has proved particularly impressive in the polymerization of acrylic acid which is at least partly present as sodium acrylate.

It thus amounts to a preferred embodiment of the invention when, in the process of the present invention, monomer a) is acrylic acid present at least partly in the form of sodium acrylate. Useful monomers will be described more particularly hereinbelow.

In principle, the customary crosslinkers and crosslinker quantities can be used in the polymerization in the context of the present invention. This will be more particularly discussed hereinbelow. It amounts to a preferred embodiment of the invention for the monomer solution or suspension to comprise at least 0.1% by weight of crosslinker b), based on unneutralized monomer a).

It is further in accordance with a preferred embodiment of the invention for a surface-postcrosslinking operation to be carried out as part of the process according to the present invention. This too will be more particularly described herein below.

It is further preferable for the preferably surface-postcrosslinked polymer to be subjected to a further treatment, preferably a surface treatment, in particular by addition of at least one aftertreating agent. This corresponds to an aftertreatment of the possibly surface-postcrosslinked polymer, preferably with at least one aftertreating agent. Suitable aftertreating agents are, in particular, substances that are added to the polymer in order to change its properties in a desired direction and/or to facilitate its processability. A person skilled in the art is well aware of suitable aftertreating agents from the field of superabsorbent technology. They include, for example, anti-dust agents, for example polyols and/or polyalkylene glycols, anti-caking agents, for example Sipernats, Aerosils, cationic surfactants, e.g. quaternary ammonium or phosphonium salts, odor control agents, e.g., zeolites, bentonites, silica, cyclodextrins, scents, antimicrobial actives or oxidizing agents.

In principle, the processing aid which is usable, within the meaning of the aforementioned explanations, according to the present invention can be used in all customary processes for producing water-absorbing polymeric particles.

Although the manufacture of water-absorbing polymeric particles is well known per se, the manufacturing process will now be more particularly described because the herein below described preferred embodiments lead to particularly good results as regards the solution for attaining the desired object.

The process of the present invention, as already noted, comprises the polymerization of a monomer solution or suspension comprising
    a) at least one ethylenically unsaturated acid-functional monomer which is optionally present at least partly in salt form,
    b) at least one crosslinker,
    c) at least one initiator,
    d) optionally one or more ethylenically unsaturated monomers copolymerizable with the monomers recited under a),
    e) optionally one or more water-soluble polymers,
    f) water,
    g) optionally additives and/or active substances.

The monomers a) are preferably water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfural, 0.0001% by weight of maleic anhydride, 0.0003% by weight of diacrylic acid and 0.0050% by weight of hydroquinone monomethyl ether. The proportion of acrylic acid and/or salts thereof in the total amount of monomers a) is preferably at least 50 mol %, more preferably at least 90 mol %, most preferably at least 95 mol %. The monomers a) can typically comprise polymerization inhibitors, preferably hydroquinone monoethers, as storage stabilizers.

The monomer solution can comprise preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight of hydroquinone monoethers, each based on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are for example compounds having at least two groups suitable for crosslinking Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b) for example.

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine. Very particularly preferred crosslinkers b) are the polyethoxylated and/or -propoxylated glycerols which have been esterified with acrylic acid or methacrylic acid to give di- or triacrylates, as described, for example, in WO 2003/104301 A1.

Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05% to 1.5% by weight, more preferably 0.1% to 1% by weight, most preferably 0.3% to 0.6% by weight, based in each case on monomer a). With rising crosslinker content, centrifuge retention capacity (CRC) falls and the absorption under a pressure passes through a maximum.

Initiators c) used may be all compounds which generate free radicals under the polymerization conditions, for example thermal initiators, redox initiators or photoinitiators. Suitable redox initiators are for example sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution can be used. The water content of the monomer solution is preferably from 40% to 75% by weight, more preferably from 45% to 70% by weight and most preferably from 50% to 65% by weight. It is also possible to use monomer suspensions, i.e. monomer solutions with excess monomer a), for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable additives and/or active substances for optional inclusion in the monomer solution or suspension are substances that are able to change the properties of the resultant polymers in a desired direction, that are capable of facilitating the processability thereof or that are capable of endowing the polymer with an additional function. Resort may be had here to any additives and/or active substances customary from the prior art.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1 for example. Polymerization on a belt is described, for example, in DE 38 25 366 A1 and U.S. Pat. No. 6,241,928. Polymerization in a belt reactor forms a polymer gel which has to be comminuted in a further process step, for example in an extruder or kneader. However, it is also possible to dropletize an aqueous monomer solution and to polymerize the droplets obtained in a heated carrier gas stream. It is possible here to combine the process steps of polymerization and drying, as described in WO 2008/040715 A2 and WO 2008/052971 A1. The acid groups of the resulting polymer gels have typically been partly neutralized. Neutralization is preferably carried out at the monomer stage. This is typically accomplished by mixing in the neutralizing agent as an aqueous solution or preferably also as a solid. The degree of neutralization is preferably from 25 to 85 mol %, for "acidic" polymer gels more preferably from 30 to 60 mol %, most preferably from 35 to 55 mol %, for "neutral" polymer gels more preferably from 65 to 80 mol %, most preferably from 70 to 75 mol %, and the customary neutralizing agents may be used, preferably alkali metal hydroxides, alkali metal oxides, alkali metal carbonates or alkali metal bicarbonates and also mixtures thereof. Ammonium salts such as the salt of triethanolamine can also be used instead of alkali metal salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent directly to the monomer solution and setting the desired final degree of neutralization only after the polymerization, at the polymer gel stage. When the polymer gel is at least partly neutralized after the polymerization, the polymer gel is preferably comminuted mechanically, for example by means of an extruder, in which case the neutralizing agent can be sprayed, sprinkled or poured on and then carefully mixed in. For this purpose, the gel material obtained can be extruded several times more for homogenization.

The polymer gel can then preferably be dried with a belt dryer until the residual moisture content is preferably 0.5 to 15% by weight, more preferably 1 to 10% by weight and most preferably 2 to 8% by weight, the residual moisture content being determined by EDANA (European Disposables and Nonwovens Association) recommended test method No. WSP 230.2-05 "Moisture Content". The EDANA test methods are obtainable, for example, from EDANA, Avenue Eugene Plasky 157, B-1030 Brussels, Belgium.

In the case of too high a residual moisture content, the dried polymer gel can have too low a glass transition temperature Tg and can then be processed further only with difficulty. In the case of too low a residual moisture content, the dried polymer gel can be too brittle and, in the subsequent comminution steps, undesirably large amounts of polymeric particles with too low a particle size ("fines") can be obtained. The solids content of the gel before the drying is preferably from 25% to 90% by weight, more preferably from 35% to 70% by weight and most preferably from 40% to 60% by weight. However, a fluidized bed dryer or a paddle dryer may optionally also be used for drying purposes.

Thereafter, the dried polymer gel is ground and classified, and the apparatus used for grinding may typically be single- or multistage roll mills, preferably two- or three-stage roll mills, cutting mills, ultracentrifuge mills, pin mills, hammer mills or vibratory mills.

The mean particle size of the polymeric particles removed as the product fraction is preferably at least 200 μm, more preferably from 250 to 600 μm and very particularly from 300 to 500 μm. The mean particle size of the product fraction may be determined by means of EDANA (European Disposables and Nonwovens Association) recommended test method No. WSP 220.2-05 "Particle Size Distribution", where the proportions by mass of the screen fractions are plotted in cumulated form and the mean particle size is determined graphically. The median particle size here is the mesh size value at which a cumulative 50% by weight is found.

The proportion of particles having a particle size of at least 150 μm is preferably at least 90% by weight, more preferably at least 95% by weight, most preferably at least 98% by weight.

Polymeric particles having too low a particle size lower the permeability. Therefore, the proportion of excessively small polymeric particles ("fines") should be small. Excessively small polymeric particles are therefore typically separated off and recycled into the process. This is preferably done before, during or immediately after the polymerization, i.e. before the drying of the polymer gel. The excessively small polymeric particles can be moistened with water and/or aqueous surfactant before or during the recycling.

It is also possible to remove excessively small polymeric particles in later process steps, for example after the surface postcrosslinking or another coating step. In this case, the excessively small polymeric particles recycled are surface postcrosslinked or coated in another way, for example with fumed silica.

If a kneading reactor is used for polymerization, the excessively small polymeric particles are preferably added during the last third of the polymerization.

If the excessively small polymeric particles are added at a very early stage, for example actually to the monomer solution, this lowers the centrifuge retention capacity (CRC) of the resulting water-absorbing polymeric particles. However, this can be compensated, for example, by adjusting the amount of crosslinker b) used.

If the excessively small polymeric particles are added at a very late stage, for example not until an apparatus connected downstream of the polymerization reactor, for example an extruder, the excessively small polymeric particles can be incorporated into the resulting polymer gel only with difficulty. Insufficiently incorporated, excessively small polymeric particles are, however, detached again from the dried polymer gel during the grinding, are therefore removed again in the course of classification and increase the amount of excessively small polymeric particles to be recycled.

The proportion of particles having a particle size of at most 850 μm is preferably at least 90% by weight, more preferably at least 95% by weight, most preferably at least 98% by weight.

Polymeric particles having too high a particle size lower the free swell rate. Therefore, the proportion of excessively large polymeric particles should likewise be small. Excessively large polymeric particles are therefore typically separated off and recycled into the grinding of the dried polymer gel.

To further improve the properties, the polymeric particles can be surface postcrosslinked. Suitable surface postcrosslinkers are compounds which comprise groups which can form covalent bonds with at least two carboxylate groups of the polymeric particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or B-hydroxyalkylamides, as described in DE 102 04 938 A1 and U.S. Pat. No. 6,239,230. Additionally described as suitable surface postcrosslinkers are cyclic carbonates in DE 40 20 780 C1, 2-oxazolidone and derivatives thereof, such as 2-hydroxyethyl-2-oxazolidone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidones in DE 198 54 574 A1, cyclic ureas in DE 102 04 937 A1, bicyclic amido acetals in DE 103 34 584

A1, oxetanes and cyclic ureas in EP 1 199 327 A2 and morpholine-2,3-dione and derivatives thereof in WO 2003/031482 A1. Preferred surface postcrosslinkers are ethylene carbonate, ethylene glycol diglycidyl ether, reaction products of polyamides with epichlorohydrin and mixtures of propylene glycol and 1,4-butanediol. Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001% to 2% by weight, more preferably 0.02% to 1% by weight and most preferably 0.05% to 0.75% by weight, based in each case on the polymeric particles.

In a preferred embodiment of the present invention, polyvalent cations are applied to the particle surface in addition to the surface postcrosslinkers before, during and/or after the surface postcrosslinking. The polyvalent cations usable are, for example, divalent cations such as the cations of zinc, magnesium, calcium and strontium, trivalent cations such as the cations of aluminum, tetravalent cations such as the cations of titanium and zirconium. Possible counterions are for example chloride, bromide, sulfate, hydrogensulfate, carbonate, hydrogencarbonate, nitrate, phosphate, hydrogenphosphate, dihydrogenphosphate and carboxylates, such as acetate and lactate. Aluminum sulfate and aluminum lactate are preferred. Apart from metal salts, it is also possible to use polyamines as polyvalent cations. The amount of polyvalent cation used is, for example, 0.001% to 1.5% by weight, preferably 0.005% to 1% by weight and more preferably 0.02% to 0.8% by weight, based in each case on the polymeric particles.

The surface postcrosslinking is typically performed in such a way that a solution of the surface postcrosslinker is applied to, preferably sprayed onto, the dried polymeric particles. After the spray application, the polymeric particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers have a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. It is possible to adjust the penetration depth of the surface postcrosslinker into the polymeric particles via the content of nonaqueous solvent or total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact dryers, more preferably paddle dryers, most preferably disk dryers. Suitable dryers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed dryers may also be used. The drying can be effected in the mixer itself, by heating the jacket or blowing in warm air. Equally suitable is a downstream dryer, for example a shelf dryer, a rotary tube oven or a heatable screw. It is particularly advantageous to effect mixing and drying in a fluidized bed dryer.

Preferred drying temperatures are in the range of 100 to 250° C., preferably 120 to 220° C., more preferably 130 to 210° C. and most preferably 150 to 200° C. The preferred residence time at this temperature in the reaction mixer or dryer is preferably at least 10 minutes, more preferably at least 20 minutes, most preferably at least 30 minutes, and typically at most 60 minutes.

Subsequently, the surface-postcrosslinked polymeric particles can be classified again, with removal of excessively small and/or excessively large polymeric particles and recycling into the process.

The preferably surface-postcrosslinked polymeric particles may be aftertreated to further improve their properties, preferably by aftertreatment, in particular coating and/or remoistening, with an aftertreating agent.

The optional remoisturizing is preferably performed at 30 to 80° C., more preferably at 35 to 70° C., most preferably at 40 to 60° C. At excessively low temperatures, the water-absorbing polymeric particles tend to form lumps, and, at higher temperatures, water already evaporates to a noticeable degree. The amount of water used for the optional remoistening is preferably from 1 to 10% by weight, more preferably from 2 to 8% by weight and most preferably from 3 to 5% by weight. The optional remoistening increases the mechanical stability of the polymeric particles and reduces their tendency to static charging. Suitable optional coatings for improving the free swell rate and permeability (SFC) are, for example, inorganic inert substances, such as water-insoluble metal salts, organic polymers, cationic polymers and di- or polyvalent metal cations. Suitable optional coatings for dust binding are, for example, polyols. Suitable optional coatings for counteracting the undesired caking tendency of the polymeric particles are, for example, fumed silica, such as Aerosil® 200, and surfactants, such as Span® 20.

The water-absorbing polymeric particles have a moisture content of preferably 1 to 15% by weight, more preferably 2 to 10% by weight and most preferably 3 to 5% by weight, the moisture content being determined by EDANA (European Disposables and Nonwovens Association) recommended test method No. WSP 230.2-05 "Moisture Content".

The water-absorbing polymeric particles advantageously resulting in the context of this invention have a centrifuge retention capacity (CRC) of typically at least 15 g/g, preferably at least 20 g/g, more preferably at least 22 g/g, especially preferably at least 24 g/g and most preferably at least 26 g/g. The centrifuge retention capacity (CRC) of the water-absorbing polymeric particles advantageously resulting in the context of this invention is typically less than 60 g/g. The centrifuge retention capacity (CRC) is determined by EDANA (European Disposables and Nonwovens Association) recommended test method No. WSP 241.3-10 "Centrifuge Retention Capacity". The water-absorbing polymeric particles advantageously resulting in the context of this invention have an absorption under a pressure of 49.2 g/cm$^2$ (0.7 psi) of typically at least 15 g/g, preferably at least 20 g/g, more preferably at least 22 g/g, especially preferably at least 23.5 g/g and most preferably at least 25 g/g. The absorption under a pressure of 49.2 g/cm$^2$ (0.7 psi) of the water-absorbing polymeric particles is typically less than 35 g/g. Absorption Against Pressure (AAP), specifically against a pressure of 49.2 g/cm$^2$ (0.7 psi), is determined in accordance with EDANA method No. WSP242.3-10.

In the context of the present invention, in one preferred embodiment of the invention, the polymerization is carried out in a kneader with the aminopolycarboxylic acid and/or its salt, in particular the EDDS, being added to the monomer solution or suspension before the polymerization, and/or to the contents of the kneader during the polymerization.

In a further preferred embodiment of the invention, the kneader is preferably equipped with at least two parallel shafts and preferably has elements on at least one shaft to transport the contents of the kneader in parallel with the shafts, from a feed section to an output section.

The kneader in one preferred embodiment of the invention may further be used in batch operation.

It has further turned out to be advantageous when, in one preferred embodiment of the invention, the iron ion content of the monomer solution or suspension is below 5 ppm, preferably below 3 ppm and more preferably below 1 ppm.

The present invention further provides water-absorbing polymeric particles obtainable by a process of the present invention, as described above. In one preferred embodiment of the invention, the water-absorbing polymeric particles of the present invention have (a) a centrifuge retention capacity (CRC) of at least 30 g/g,
(b) an Absorption Against Pressure (AAP 0.7 psi) of at least 20 g/g.

In a further preferred embodiment of the invention, the proportion of water-absorbing polymeric particles according to the invention having a particle size of at least 150 μm is at least 90% by weight, more preferably at least 95% by weight, most preferably at least 98% by weight, and the proportion of water-absorbing polymeric particles according to the invention having a particle size of at most 850 μm is preferably at least 90% by weight, more preferably at least 95% by weight, most preferably at least 98% by weight, based in each case on the total amount of the water-absorbing polymeric particles according to the invention.

The present invention makes possible the provision of articles comprising water-absorbing polymeric particles. The invention thus further provides an article, in particular a liquid-imbibing hygiene article, comprising water-absorbing polymeric particles of the present invention.

Preferred articles of this type include, for example, any incontinence aids, such as, in particular, diapers and also hygiene articles, such as, in particular, sanitary napkins and tampons.

The present invention further provides for the use of at least one chelating agent from the group of aminopolycarboxylic acids, preferably comprising ethylenediaminedisuccinic acid, ethylenediaminetetraacetic acid, diethylenetriaminetetraacetic acid, glutamic acid N,N diacetic acid, methylglycinediacetic acid and/or salts thereof, wherein ethylenediaminedisuccinic acid and/or a salt thereof are preferable, as processing aids in the manufacture of water-absorbing polymeric particles, preferably by polymerizing a monomer solution or suspension comprising a) at least one ethylenically unsaturated acid-functional monomer which is optionally at least partly present as salt, b) at least one crosslinker and c) at least one initiator and also water, for
i) controlling the polymerization kinetics,
ii) reducing the heat evolution in the start phase following initiation of the polymerization, preferably in the first 600 seconds after initiation of the polymerization,
iii) reducing the uncrosslinked soluble fractions in the polymerization end product,
iv) improving the CRC/AAP ratio in the polymerization end product,
and/or
v) improving the gel flowability, gel tackiness and/or gel processing of the undried polymer.

EXAMPLES

Test Methods:

All test methods are in principle, unless stated otherwise, conducted in the context of this invention at an ambient temperature of 23±2° C. and a relative air humidity of 50±10%. The water-absorbing polymeric particles are mixed thoroughly before the measurement.

Centrifuge Retention Capacity (CRC).

The centrifuge retention capacity was determined by EDANA (European Disposables and Nonwovens Association) recommended test method No. WSP 241.3-10 "Centrifuge retention capacity".

Absorption against a pressure of 0.7 psi (AAP):

Absorption Against Pressure (AAP), here of 0.7 psi, was determined in accordance with Edana Method No. WSP242.3-10.

Residual monomer content:

The residual monomer content of the superabsorbent particles was determined in accordance with EDANA standard test method No. WSP210.3-10.

Soluble fractions, 16 h—value:

The proportion of the superabsorbent particles which is contributed by the 16-hour soluble fractions was determined in accordance with EDANA standard test method No. WSP270.3-10.

Determining the maximum differential pressure at the kneader shafts and the maximum temperature during the polymerization:

The temperature of the polymer was determined throughout the entire residence time of the polymer in the reactor by means of a thermosensor projecting into the reaction space. The maximum value occurring during the polymerization reaction was determined. The differential pressure at the shafts of the kneader reactor was determined via a pressure pick-up and is a measure of the torque and the shearing forces in the reaction space. An elevated differential pressure is indicative of increased torques and thus shearing forces in the reaction space. The maximum value occurring during the residence time of the polymer in the kneader reactor was determined.

Manufacturing Procedure:

a) Precursor Polyacrylate

A monomer solution consisting of 2400.00 g of acrylic acid, 2853.37 g of 32% aqueous sodium hydroxide solution, 1510.82 g of completely ion-free water, 15.99 g of 60% polyethylene glycol 600 solution and an aqueous solution of a chelating agent was freed from dissolved oxygen by purging with nitrogen. The nitrogen purging was performed for about 10 minutes. Shortly before being transferred into the kneading reactor, the monomer solution was admixed with initially 23.99 g of sodium sulfate and 197.84 g of partially neutralized surface-postcrosslinked polyacrylic acid having an average particle size of <150 μm (corresponds to the fines fraction of typical polyacrylate particles) under continued inert gas purging. This was followed under continued agitation by the addition of 6.95 g of 69% monoallyl ether polyethylene glycol 450 monoacrylate solution and also 2.40 g of 15[EO] trimethylolpropane triacrylate.

This was followed by the transfer of the monomer solution in inert gas countercurrent into the polymerization reactor heated to 35° C. by jacket and shaft heating. The polymerization reactor consisted of a two-shaft, corotating, discontinuously operated kneader reactor from LIST AG (CH-4422 Arisdorf, Switzerland). During the transportation of the monomer solution by a slightly negative pressure in the system, the shaft speed was 60 rpm, as also with the intake of 359.82 g of 10% sodium carbonate solution. The system was then pressure relieved and blanketed with an inert gas and the addition of 35.98 g of a 10% aqueous sodium peroxodisulfate solution and 17.99 g of a 6% aqueous hydrogen peroxide solution took place.

The polymerization was initiated by the addition of 85.67 g of a 0.70% aqueous ascorbic acid solution. Directly following the initiation of the reaction the jacket and shaft heating was controlled to the target value of 75° C. The shafts of the reactor were throttled at 25 revolutions per minute. An exothermic polymerization reaction took place and the inert gas flushing was ended. The residence time of the reaction mixture was 20 minutes. Shortly before the reactor was emptied, the jacket and shaft temperature was controlled to a target value of 35° C. Without further comminution steps, the hydrogel formed was dried in portions in a laboratory forced air drying cabinet at 190° C. for 30 minutes.

The dried polymer was subsequently comminuted in a cutting mill (2 mm) and the particle sizes of the comminuted dried superabsorbent from 150 μm to 850 μm were recovered by sieving.

b) Surface Postcrosslinking:

A subsequent surface-postcrosslinking operation was performed using dried, ground and screened-off polymeric particles (=precursor material) from the manufacturing procedure described above.

To this end, the surface-postcrosslinking solution consisting of ethylene carbonate/water (1 and, respectively, 3 weight percent based on superabsorbent mass) was sprayed onto the precursor material using a disposable syringe and mixed in a Krupps blender for about 1 minute. This was followed by drying/surface postcrosslinking in a laboratory drying cabinet at 180° C./30 minutes. A renewed classification of the fractions took place, and also a homogenization of the generated sample of superabsorbent.

The examples which follow were carried out under recourse to the aforementioned manufacturing procedure:
Reference (batch without addition of chelating agents)
No aqueous chelating agent solution was added.

Example 1: (Batch with DTPA Pentasodium Salt as Processing Aid)

The chelating agent was added to the monomer solution in the form of 1.19 g of a 40.2% by weight aqueous solution of sodium diethylenetriaminepentaacetate salt (Versenex® 80E ex Dow).

Example 2a (Batch with EDTA Tetrasodium Salt=Trilon® B Liquid ex BASF as Processing Aid)

The chelating agent was added to the monomer solution in the form of 0.85 g of a 42.5% by weight aqueous solution of sodium ethylenediaminetetraacetate salt (Trilon® B liquid ex BASF).

Example 2b (Batch with EDTA Tetrasodium Salt=Trilon® B Liquid ex BASF as Processing Aid)

The chelating agent was added to the monomer solution in the form of 1.70 g of a 42.5% by weight aqueous solution of sodium ethylenediaminetetraacetate salt (Trilon® B liquid ex BASF).

Example 2c (Batch with EDTA Tetrasodium Salt=Trilon® B Liquid ex BASF as Processing Aid)

The chelating agent was added to the monomer solution in the form of 5.11 g of a 42.5% by weight aqueous solution of sodium ethylenediaminetetraacetate salt (Trilon® B liquid ex BASF).

Example 3a (Batch with MGDA Trisodium Salt=Trilon® M Liquid ex BASF as Processing Aid)

The chelating agent was added to the monomer solution in the form of 0.65 g of a 40.0% by weight aqueous solution of sodium methylglycinediacetate (Trilon® M liquid ex BASF).

Example 3b (Batch with MGDA Trisodium Salt=Trilon® M Liquid ex BASF as Processing Aid)

The chelating agent was added to the monomer solution in the form of 6.48 g of a 40.0% by weight aqueous solution of sodium methylglycinediacetate (Trilon® M liquid ex BASF).

Example 4a (Batch with GLDA Trisodium Salt=Dissolvine® GL-47-S ex AkzoNobel as Processing Aid)

The chelating agent was added to the monomer solution in the form of 0.71 g of a 47.0% by weight aqueous solution of tetrasodium N,N-bis(carboxymethyl)-L-glutamate (Dissolvine® GL-47-S ex AkzoNobel).

Example 4b (Batch with GLDA Trisodium Salt=Dissolvine® GL-47-S ex AkzoNobel as Processing Aid)

The chelating agent was added to the monomer solution in the form of 2.86 g of a 47.0% by weight aqueous solution of tetrasodium N,N-bis(carboxymethyl)-L-glutamate (Dissolvine® GL-47-S ex AkzoNobel).

Example 4c (Batch with GLDA Trisodium Salt=Dissolvine® GL-47-S ex AkzoNobel as Processing Aid)

The chelating agent was added to the monomer solution in the form of 10.21 g of a 47.0% by weight aqueous solution of tetrasodium N,N-bis(carboxymethyl)-L-glutamate (Dissolvine® GL-47-S ex AkzoNobel).

Example 5a (Batch with EDDS Tetrasodium Salt=Enviomet® C140 ex Innospec Specialty Chemicals as Processing Aid)

The chelating agent was added to the monomer solution in the form of 1.37 g of a 35.0% by weight aqueous solution of trisodium ethylenediaminedisuccinate (Enviomet® C140 ex Innospec Specialty Chemicals).

Example 5b (Batch with EDDS Tetrasodium Salt=Enviomet® C140 ex Innospec Specialty Chemicals as Processing Aid)

The chelating agent was added to the monomer solution in the form of 2.40 g of a 35.0% by weight aqueous solution of trisodium ethylenediaminedisuccinate (Enviomet® C140 ex Innospec Specialty Chemicals).

Example 5c (Batch with EDDS Tetrasodium Salt=Enviomet® C140 ex Innospec Specialty Chemicals as Processing Aid)

The chelating agent was added to the monomer solution in the form of 5.14 g of a 35.0% by weight aqueous solution of trisodium ethylenediaminedisuccinate (Enviomet® C140 ex Innospec Specialty Chemicals).

Example 5d (Batch with EDDS Tetrasodium Salt=Enviomet® C140 ex Innospec Specialty Chemicals as Processing Aid)

The chelating agent was added to the monomer solution in the form of 13.71 g of a 35.0% by weight aqueous solution of trisodium ethylenediaminedisuccinate (Enviomet® C140 ex Innospec Specialty Chemicals).

| Example | Maximum reaction temperature [° C.] | Maximum hydraulic differential pressure at kneader shaft [bar] | CRC, WSP241.3 [g/g] | AAP 0.7 psi, WSP242.3 [g/g] | Soluble fractions 16 h, WSP 270.3 [%] of precursor material | Residual monomers, WSP210.3 [mg/kg] of precursor material |
| --- | --- | --- | --- | --- | --- | --- |
| reference | 82 | 137 | 33.4 | 17.7 | 30.2 | 350 |
| 1 | 78 | 62 | 31.5 | 23.1 | 19.2 | 1710 |
| 2a | 78 | 96 | 33.9 | 16.0 | 33.0 | 705 |
| 2b | 77 | 85 | 34.8 | 19.1 | 29.3 | 690 |
| 2c | 79 | 87 | 33.7 | 17.6 | 31.2 | 655 |
| 3a | 80 | 99 | 31.9 | 19.2 | 26.1 | 970 |
| 3b | 78 | 77 | 31.6 | 19.7 | 18.5 | 1510 |
| 4a | 79 | 89 | 32.6 | 20.6 | 23.0 | 1140 |
| 4b | 78 | 72 | 32.2 | 21.7 | 20.0 | 1560 |
| 4c | 78 | 66 | 32.3 | 23.9 | 19.8 | 1340 |
| 5a | 78 | 70 | 32.5 | 22.6 | 21.4 | 1370 |
| 5b | 79 | 62 | 32.9 | 24.2 | 20.7 | 1410 |
| 5c | 82 | 61 | 32.1 | 24.2 | 19.8 | 1660 |
| 5d | 86 | 60 | 31.3 | 25.5 | 15.8 | 2430 |

The invention claimed is:

1. A process for producing water-absorbing polymeric particles by polymerizing a monomer solution or suspension consisting of
   a) at least one ethylenically unsaturated acid-functional monomer which is optionally present at least partly in salt form,
   b) at least one crosslinker,
   c) at least one initiator,
   d) one or more ethylenically unsaturated monomers copolymerizable with the monomers mentioned under a),
   e) one or more water-soluble polymers,
   f) water,
   g) additives and/or active substances,
   wherein said process further comprises drying the polymer obtained, and grinding the dried polymer and sieving the ground polymer, and surface-postcrosslinking the dried, and ground and sieved polymer, and aftertreating the surface-postcrosslinked polymer with at least one aftertreating agent,
   wherein the polymerization is carried out in the presence of a chelating agent comprising ethylenediaminedisuccinic acid and/or salts thereof and in a kneader,
   wherein the addition of the chelating agent is to the monomer solution or suspension before the polymerization and/or the addition of the chelating agent is to the contents of the kneader during the polymerization,
   wherein the chelating agent is added to the monomer solution or suspension in an overall amount of at least 5 ppm based on the amount of unneutralized monomer;
   wherein the chelating agent controls the polymerization kinetics; and
   wherein the resulting water-absorbing polymeric particles have an absorption under pressure of 49.2 g/cm$^2$ (0.7 psi) of at least 22 g/g, as determined according to EDANA Method No. WSP 241.3-10.

2. The process according to claim 1, wherein the chelating agent is ethylenediaminedisuccinic acid and/or a salt thereof, which is added before and/or during the polymerization.

3. The process according to claim 1, wherein the chelating agent is added to the monomer solution or suspension in solid, particulate form and/or in the form of an aqueous solution.

4. The process according to claim 1, wherein the monomer a) is acrylic acid present at least partly in the form of sodium acrylate.

5. The process according to claim 1, wherein the monomer solution or suspension comprises at least 0.1% by weight of crosslinker b), based on unneutralized monomer a).

6. The process according to claim 1, wherein the surface-postcrosslinked polymer is subjected to a further treatment, a surface treatment, in particular by addition of at least one aftertreating agent.

7. The process according to claim 1, wherein the kneader is equipped with at least two parallel shafts and has elements on at least one shaft to transport the contents of the kneader in parallel with the shafts, from a feed section to an output section.

8. The process according to claim 1, characterized in that the kneader is used in batch operation.

9. The process according to claim 1, characterized in that the iron ion content of the monomer solution or suspension is below 5 ppm.

* * * * *